(12) United States Patent
Hilbert et al.

(10) Patent No.: US 9,645,378 B2
(45) Date of Patent: May 9, 2017

(54) MICROSCOPE AND METHOD FOR SPIM MICROSCOPY (71) Applicant: Carl Zeiss Microscopy GmbH, Jena (DE)

(72) Inventors: Wiebke Hilbert, Jena (DE); Helmut Lippert, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 124 days.

(21) Appl. No.: 14/434,940

(22) PCT Filed: Oct. 9, 2013

(86) PCT No.: PCT/EP2013/071077
§ 371 (c)(1),
(2) Date: Apr. 10, 2015

(87) PCT Pub. No.: WO2014/056992
PCT Pub. Date: Apr. 17, 2014

(65) Prior Publication Data
US 2015/0286042 A1 Oct. 8, 2015

(30) Foreign Application Priority Data
Oct. 12, 2012 (DE) .................. 10 2012 020 240

(51) Int. Cl.
*G02B 21/06* (2006.01)
*G02B 21/00* (2006.01)
(Continued)

(52) U.S. Cl.
CPC .......... *G02B 21/06* (2013.01); *G01N 21/6458* (2013.01); *G01N 21/6486* (2013.01);
(Continued)

(58) Field of Classification Search
CPC .......... G01N 21/6458; G01N 21/6486; G01N 2201/02; G01N 2201/06113;
(Continued)

(56) References Cited

U.S. PATENT DOCUMENTS 8,970,950 B2 3/2015 Stelzer
2007/0109633 A1 5/2007 Stelzer
(Continued)

FOREIGN PATENT DOCUMENTS

DE 10257423 6/2004
DE 10 2007017598 10/2008
(Continued)

OTHER PUBLICATIONS

International Search Report (PCT/EP2013/071077) dated Dec. 5, 2013.
(Continued)

*Primary Examiner* — Mark R Gaworecki
(74) *Attorney, Agent, or Firm* — Haug Partners LLP (57) ABSTRACT

Method and microscope for SPIM microscopy, wherein, in a first step, with reference to a sample to be examined, a calibration is carried out in that the actual position of the light sheet in different sample planes is detected and stored depending on the position in the sample and, in a second step, the stored position of the light sheet is utilized during observation and/or detection of the sample based on the values stored in the first step to correct the position of the light sheet relative to the focal plane of the detection objective and/or, during the displacement of the sample, an adjustment of the position of the light sheet relative to the focal plane of the detection objective is carried out such that the light sheet executes a relative movement in at least one direction relative to the sample and/or the detection objective.

20 Claims, 6 Drawing Sheets

(51) Int. Cl.
   *G02B 21/24* (2006.01)
   *G01N 21/64* (2006.01)
   *G02B 21/36* (2006.01)
   *G02B 21/16* (2006.01)

(52) U.S. Cl.
   CPC ....... *G02B 21/002* (2013.01); *G02B 21/0076* (2013.01); *G02B 21/16* (2013.01); *G02B 21/244* (2013.01); *G02B 21/361* (2013.01); *G02B 21/367* (2013.01); *G01N 2201/02* (2013.01); *G01N 2201/06113* (2013.01)

(58) Field of Classification Search
   CPC .. G02B 21/002; G02B 21/0076; G02B 21/06; G02B 21/16; G02B 21/244; G02B 21/361; G02B 21/367
   See application file for complete search history.

(56) References Cited

U.S. PATENT DOCUMENTS

| | | |
|---|---|---|
| 2010/0201784 A1 | 8/2010 | Lippert et al. |
| 2011/0304723 A1 | 12/2011 | Betzig |
| 2013/0094755 A1 | 4/2013 | Lippert et al. |
| 2014/0042339 A1 | 2/2014 | Stelzer et al. |

FOREIGN PATENT DOCUMENTS

| | | |
|---|---|---|
| DE | 102007045897 | 4/2009 |
| DE | 10 2010 060 121 | 4/2012 |
| WO | WO 2004/053558 | 6/2004 |
| WO | WO 2008/125204 | 10/2008 |

OTHER PUBLICATIONS

Notification of transmittal of the translation of International Preliminary Report on Patentability dated Apr. 23, 2015.
Fahrbach et al, "Rapid 3D light-sheet microscopy with a tunable lens", 2013 Optical Society of America, Aug. 30, 2013, vol. 21, No. 18., XP055089699, pp. 21010.
German Search Report for Application No. 10 2012 020 240.7 dated Jan. 16, 2013.
Greger et al. "Basic Building Units and Properties of a fluorescence Single Plane Illumination Microscope" (Greger et al., *Rev. Sci. Instr*, 78, 023705, 2007, Section II B.).
Krzic et al."Multiview Light-Sheet Microscope for Rapid in toto Imaging", (*Nat Methods* 9, 730, 2012, Suppl.).
Voie et al., "Orthogonal-plane Fluorescence Optical Sectioning: three-dimensional Imaging of Macroscopic Biological Specimens", (*Journal of Microscopy* 170, 229, 1992, Section "Illumination System").
Santi et al., "Thin-Sheet Laser Imaging Microscopy for Optical Sectioning of Thick Tissues", (*BioTechniques* 46, 287, 2009, Suppl. Mat.).
Keller et al. "Reconstmction of Zebrafish Early Embryonic Development by Scanned Light Sheet Microscopy", (*Science* 322, 1065, 2008).

MICROSCOPE AND METHOD FOR SPIM MICROSCOPY

The present application claims priority from PCT Patent Application No. PCT/EP2013/071077 filed on Oct. 9, 2013, which claims priority to German Patent Application No. DE 10 2012 020 240.7 filed on Oct. 12, 2012, the disclosures of which are incorporated herein by reference in their entirety.

FIELD OF THE INVENTION

The invention is directed to a microscope which comprises an imaging objective for imaging a sample on a detector and means for illumination of the sample with a light sheet in the focal plane of the imaging objective or in a defined plane in the vicinity of this focal plane. The means for illumination comprise an illumination source emitting preferably coherent light.

It is noted that citation or identification of any document in this application is not an admission that such document is available as prior art to the present invention.

A microscope in which the illumination beam path and detection beam path are arranged substantially perpendicular to one another and in which the sample is illuminated by a light sheet in the focal plane of the imaging objective, i.e., perpendicular to the optical axis thereof, is configured for examination of samples using the method of selective plane illumination microscopy (SPIM). In contrast to confocal scanning microscopy (LSM) in which a three-dimensional sample is scanned point by point in individual planes at different depths and the image information acquired in so doing is subsequently compiled to form a three-dimensional image of the sample, SPIM technology is based on widefield microscopy and allows the sample to be imaged on the basis of optical sections through individual planes of the sample.

The advantages of SPIM technology reside inter alia in the faster speed at which image information is acquired, the reduced risk of photobleaching of biological samples and an expanded depth of penetration of the focus in the sample.

Basically, in SPIM technology fluorophores which are contained in or introduced into the sample are excited by laser light which is shaped to form a light sheet, as it is called. A selected plane in the depth of the sample is illuminated by the light sheet and an image of this sample plane is obtained in the form of an optical section with imaging optics. The rapid reciprocating motion of a thin, rotationally symmetrical laser beam in the focal plane of the imaging optics is essentially equivalent to excitation of this kind by a static light sheet. Accordingly, the shape of a SPIM light sheet also results effectively, i.e., time-averaged over the period of observation.

SPIM technology is described, for example, in Stelzer et al., *Optics Letters* 31, 1477 (2006), Stelzer et al., *Science* 305, 1007 (2004), DE 102 57 423 A1, and WO 2004/0530558 A1.

Figure 1:
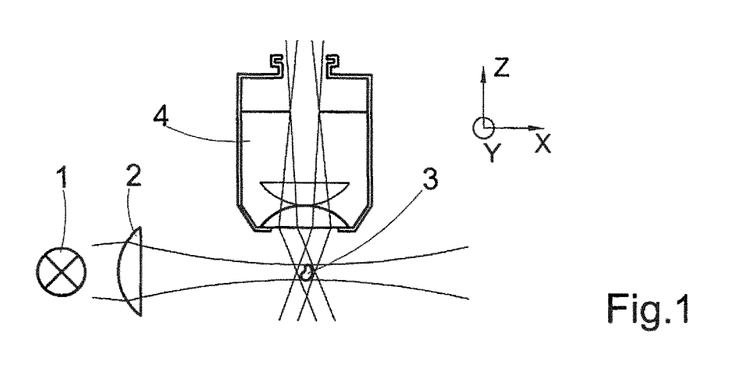
FIG. 1 shows the basic construction of a SPIM microscope.

First, FIG. 1 shows the basic construction of a SPIM microscope. The light from an illumination source 1 is shaped via illumination optics 2 to form a light sheet and is guided to a sample 3. The sample and light sheet are located in the focal plane of an imaging objective 4. The optical axis of the imaging objective 4 extends perpendicular to the direction from which the sample 3 is illuminated. The illumination optics 2 generally comprise a plurality of optical elements which collimate the coherent light of the illumination source 1 and shape a light sheet therefrom. In the prior art, the illumination optics 2 generally also have a cylindrical lens having a flat side facing the sample and a curved side facing in direction of the illumination source.

By means of a sample holder PH, shown schematically, the sample is moved in direction of the optical axis of the objective 4 by motor under control of a control unit A, for example.

The described light sheet microscopy combines optical sections with a widefield detection via a spatially resolving camera (CCD camera) in that the entire lateral focal plane (XY plane) of the detection objective is illuminated with a thin light sheet (FIG. 1). The light sheet illumination is carried out at a right angle to the detection axis (Z axis).

The sample is placed in the area of overlap of illumination and detection. Fluorescence signals which are excited by the illumination light sheet are imaged on the camera over the entire field of view of the detection objective. As a result of the right-angled illumination with a thin light sheet, only a small portion of the axial extension of the detection optics is illuminated and, therefore, an optical section is generated. In order to observe a different region in the sample, the sample is moved through the light sheet with a sample positioning unit independently from the optics. By capturing optical sections at different sample positions along the detection axis, it is possible to capture three-dimensional image stacks. These image stacks can subsequently be reconstructed to form 3D images.

For this purpose, it is necessary to capture a plurality of three-dimensional image stacks from different angles. An image stack comprises, for example, 200 images. At least four different irradiation angles are needed for a three-dimensional image.

Perfect overlapping of the illumination plane and detection plane is especially critical for good image quality and clean sectioning. Due to changing samples and refractive indices, this is a constantly recurring task from day to day.

As a result of the known relative movement of the light sheet with respect to the sample and objective, the illuminated z plane within the sample and, therefore, the sample plane that is utilized for evaluation varies during adjustment. When an adjustment procedure such as this is applied to a real sample, the z movement results in a wide variation in the data in the individual adjustment images so that it is no longer possible to evaluate the adjustment image. To a lesser extent, this problem also relates to adjustment procedures with a reference sample. However, these samples are more homogeneous so that it is rarely apparent.

A manual, user-controlled adjustment is time-consuming and requires extensive experience. In this regard, the user mostly concentrates on heavily structured image regions to simplify evaluation, although the information content of these image regions is highly dependent on the z plane of the sample. If this z plane varies during the adjustment process, this often leads to an erroneous evaluation.

Further prior art is disclosed in patent applications DE 102007017598 A1 and DE 102007045897 A1. The known adjustment methods require on the one hand a fluorescing reference object (e.g., beads, fiducials or a homogeneous fluorescing object) instead of the sample or positioning thereof in the sample. These reference objects are illuminated by the flat light sheet, and the optimal adjustment point is sought based on the contrast or PSF (e.g., in case of beads). On the other hand, in many methods a reference structure is applied to the fluorescing reference object through the illumination light. This is carried out, for example, through a grating in a plane conjugate to the object plane or through a modulation of the scanned light sheet.

Adjustment methods based on a reference sample require that the reference sample is completely identical to the real user sample with respect to all optical characteristics (refractive index, surface curvature, penetration depth, . . . ). This cannot be realized for the existing spectrum of predetermined samples. To this extent, these adjustment methods allow for deviations from the optimal adjustment. Optical effects due to inhomogeneous sample structures, e.g., different cell structures, cannot be taken into account at all. Similar effects occur when the depth of penetration into the sample medium changes greatly during the capture of an image stack.

The general light sheet adjustment according to the prior art is described, for example, in Greger et al. (Greger et al., *Rev. Sci. Instr,* 78, 023705, 2007, Section II B.). Here, a gimbal mount and telescope are used to move the light sheet alone along the z direction of the detection optics by means of an angular motion. This orientation of the illumination optics relative to the detection optics also corresponds to the older prior art according to Voie et al. (*Journal of Microscopy* 170, 229, 1992, Section "Illumination System") or Santi et al. (*BioTechniques* 46, 287, 2009, Suppl. Mat.). Krzic et al. (*Nat Methods* 9, 730, 2012, Suppl.) describe three-dimensional light sheet adjustment for a scanning light sheet by means of a "parked" laser beam which illuminates a fluorescing solution. The waist of the laser beam, inter alia, is utilized for this purpose. The use of scattered light is also described. Implementation of the light sheet adjustment through movement of the detection optics relative to the light sheet in a fluorescing solution or reference sample is also described. Keller et al. (*Science* 322, 1065, 2008, Suppl.) describe a construction with movable detection optics, but the latter are not described within the framework of a light sheet adjustment.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112), such that applicant(s) reserve the right to disclaim, and hereby disclose a disclaimer of, any previously described product, method of making the product, or process of using the product.

SUMMARY OF THE INVENTION

The invention is characterized inter alia through the features of the independent and dependent patent claims incorporated in the present disclosure.

Advantageous prerequisite for a favorable automated adjustment is the selection of the correct evaluation criterion and the applicability to the real sample instead of a reference structure.

There is no known prior art method in which the sample to be examined is used directly in light sheet adjustment, wherein it is moved jointly with the light sheet relative to the objective and detection plane.

The invention comprises particularly a movement of the light sheet and sample relative to the predetermined focal plane of the detection unit, which movement is preferably coupled via an actuating unit.

Of course, conversely, the detection objective alone can also be moved or all of the elements can be moved relative to one another so as to be coordinated via a shared actuating unit to achieve the inventive effect. If the sample is tracked after or simultaneous with an adjustment of the light sheet, the sample plane under consideration and, therefore, the basic image content remain identical. Differences in the image are brought about only through the adjustment position. The two individual movements can advantageously be adapted to one another beforehand with sufficient precision via a calibration so that a correctly coupled movement can be carried out.

Further, it is possible and advantageous for the method described in the following to determine the sample structures utilized for the adjustment by means of an alternative contrast method beforehand and to orient the sample relative to the detection means subsequently.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 2:
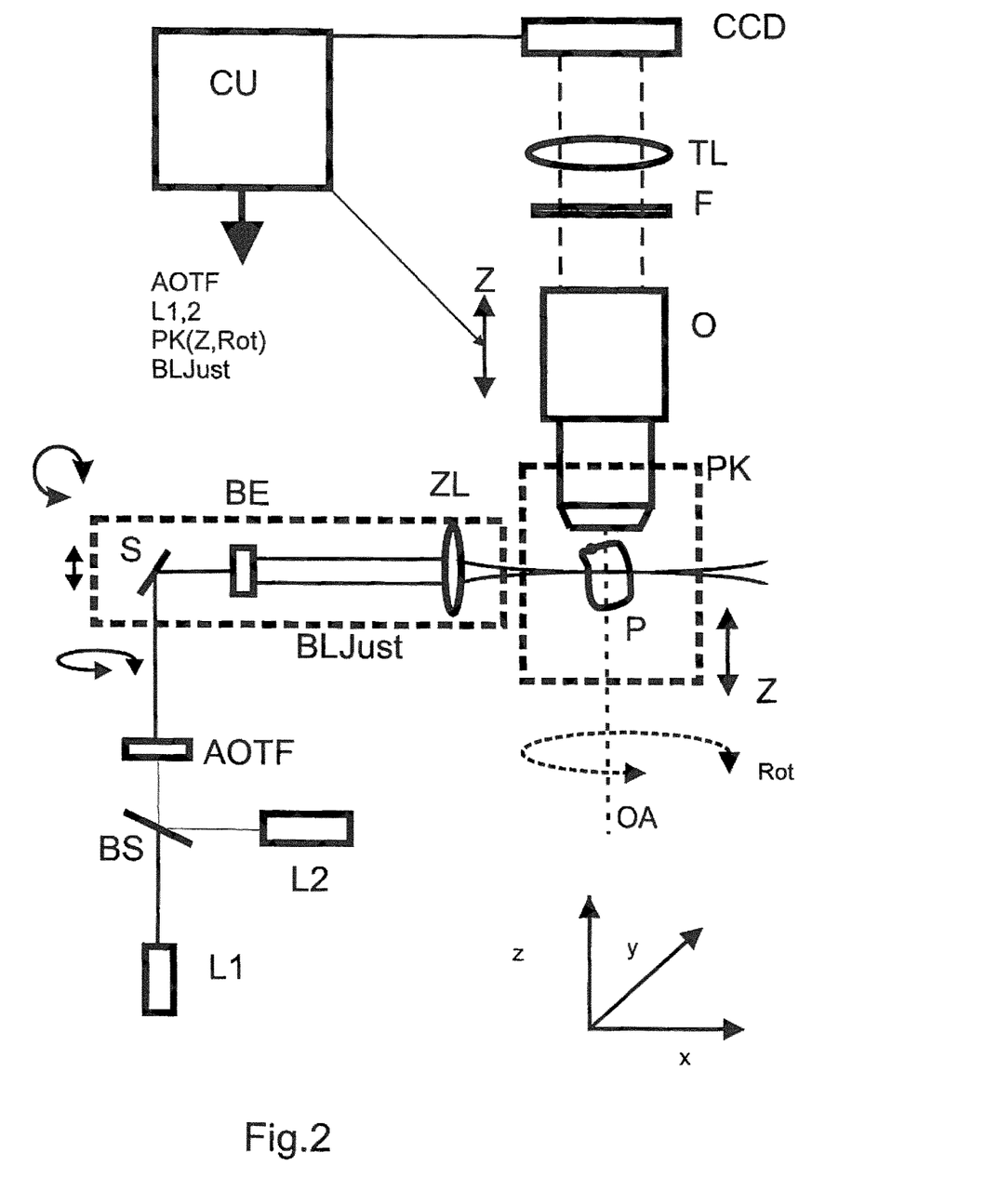
FIG. 2 shows the basic construction of a SPIM microscope for implementing the method according to the invention.

FIG. 2 shows the basic construction of a SPIM microscope for implementing the method according to the invention.

A sample P which may be located in a sample chamber PK, which sample or sample chamber is arranged so as to be displaceable in direction of a z axis and also arranged so as to be rotatable around the optical axis of the detection objective, is detected by a detection beam path which comprises a vertically adjustable detection objective O with a detection axis or optical axis which extends in Z direction and in which are arranged, in detection direction, a preferably exchangeable light filter F, a tube lens TL and a surface receiver CCD.

Substantially perpendicular to the detection axis Z, in this case in x direction, there are an illumination beam path comprising in this case two lasers L1, L2 which are coupled via a beamsplitter BS and which generate the two-dimensional light distribution penetrating the sample via an AOTF for wavelength selection and intensity adjustment, a deflecting mirror S, a beam expander BE and anamorphic optics such as, in this case, a cylindrical lens ZL for beam shaping.

Shown schematically is an adjusting unit BLjust which, for example, can adjust or tilt elements S, BE and ZL in a plurality of directions.

A z displacement of the illumination, represented by the vertical arrow, a rotation of the illumination unit around the z axis and a tilting, in this case, for example, around the y axis, are preferably carried out, wherein the center of rotation of the tilting through a coupled z displacement and rotation around the mirror axis can also lie in the sample, for example, in the optical axis OA of the detection objective.

A shared monitoring-and-control device CU, generally formed by a computer and a display unit (display), is connected to all of the adjusting devices such as the AOTF, sample chamber displacement means PK and illumination adjustment means BLJust to carry out the method according to the invention.

Figure 3:
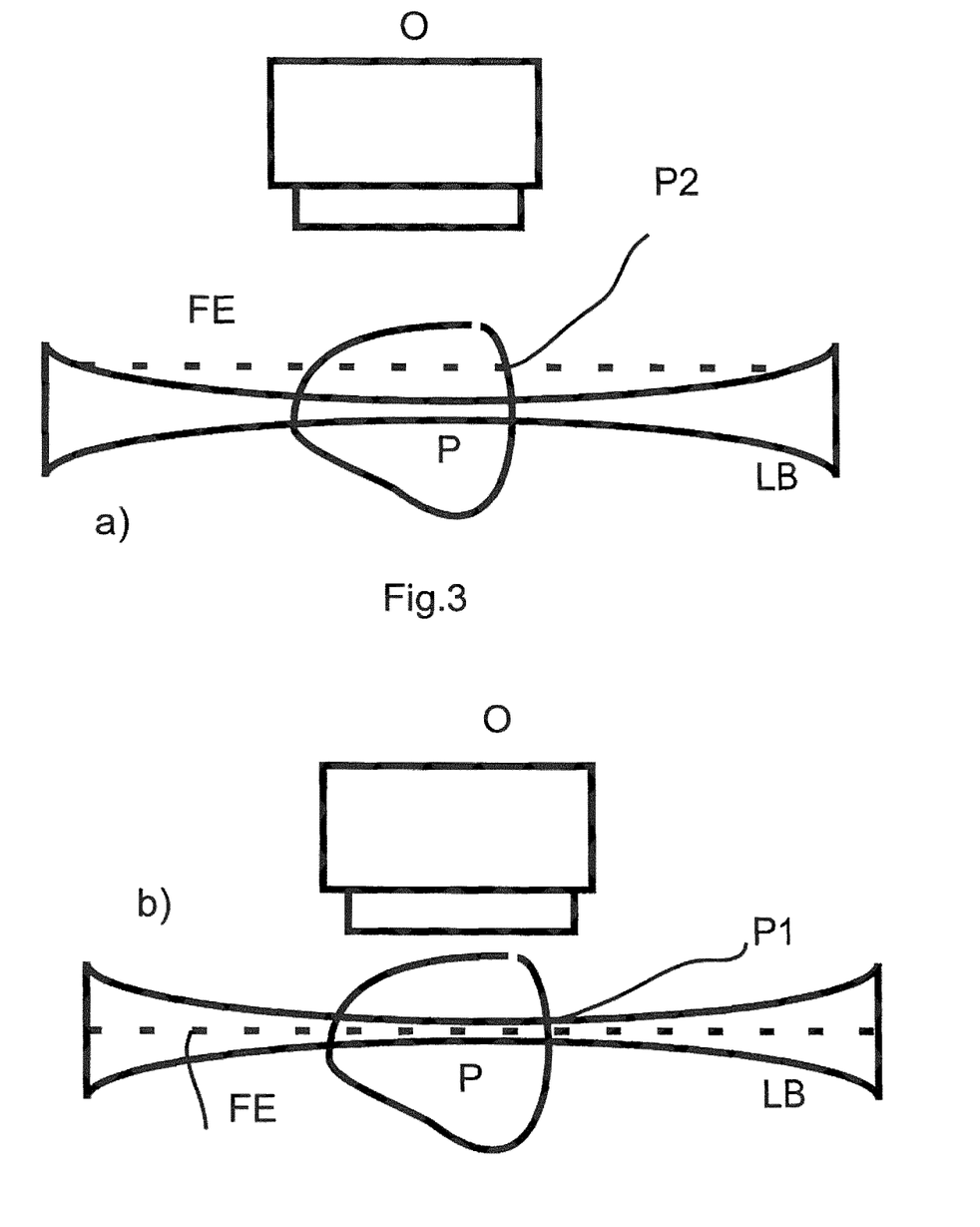
FIG. 3a shows the initial condition of a defocussed light sheet.
FIG. 3b shows the adjusted condition by means of displacing the light sheet.

The following details from FIG. 2 are shown in FIGS. 3 to 6:
- O: detection objective
- P: as sample, a tissue with tagged cell nuclei for exemplary sample planes
- K: camera image of the sample with cell nuclei
- LB: area of the light sheet illumination (e.g., Gaussian beam)
- OA: optical axis of the illumination (dotted)
- FE: focal plane of the detection optics FIGS. 3a, b show the initial condition of a defocussed light sheet in 3a) and the adjusted condition by means of displacing the light sheet in 3b). It is clear from 3a and 3b that different sample regions P1, P2 are imaged by the objective O.

The invention ensures the condition in 3b in the same way for each traversed sample plane in order to realize a perfect sample section.

The following advantageous methods are suggested for this purpose:

Method 1:

When the user focuses the sample by moving the sample or sample holder in direction of the detection axis of the objective (z axis), it may happen that the light sheet no longer lies exactly in the focal plane of the detection objective owing to the actually existing differences in the refractive index of the sample or discontinuities in the refractive index.

Therefore, a calibrating table is adopted in a calibrating step before the actual measurement of the sample. This calibrating table carries out a z adjustment for the sample that is actually used, wherein the actual position of the light sheet is detected as a function of the vertical position of the sample (and accordingly depending on the refractive index of the sample).

To this end, the respective vertical position of the light sheet is detected and stored together at its position at its adjusting means for the different focused sample regions of a real sample.

The detection of the light sheet position is carried out in the following manner, for example:

A z adjustment of the sample is carried out, and the respective z positions form a storage value, where $Z1-Zi$ ($i=1-n$).

For $Z1-Zi$, the light sheet is at least vertically adjusted, and also preferably tilted before or after (for example, by the actuating unit Cu in FIG. 2).

The adjustment and/or tilting is preferably carried out around the respective value $Zi$.

Based on focus determination and contrast analysis through the CCD in FIG. 2 (also conceivably visually by the observer) and the evaluating unit CU, the value of the highest sharpness and/or of an optimal contrast is stored (in the calibrating table) with the values of the adjusting unit BLJust in FIG. 2 set to this value by Cu so as to be associated with the respective value $Zi$, or the light sheet position adjusted in this way is also used in addition directly for a measurement.

This position determination of the light sheet at the $Zi$ values is subsequently used, when the user observes a determined z plane in the sample or when this z plane is detected, in order to carry out a corresponding correction, i.e., to set the actual light sheet position for precisely this focused sample region so that the actual light sheet always lies in the actually observed or detected focal plane in spite of the above-mentioned fluctuations in the refractive index.

Method 2:

During the displacement of the sample into a new z plane, simultaneously or immediately thereafter, the light sheet is moved relative to the sample (for example, with determination of the optimal contrast), at least in Z direction, preferably also tilted around an axis of rotation, for example, in the center of the focal plane of the detection objective.

For example, as a result of its refractive index curve, a curved surface or interface in the sample can result in the light sheet being "bent away" from a horizontal position into a tilted position. This is advantageously compensated again by the method. This can take place visually or automatically (analogous to autofocusing methods functioning with contrast adjustment).

The linking of the movements of the sample in z direction and of the light sheet displacement and the evaluation of the sample contrast is preferably carried out in the controlling-and-computing unit XX.

Methods 1 and 2 can also advantageously be applied in combination.

Figure 4:
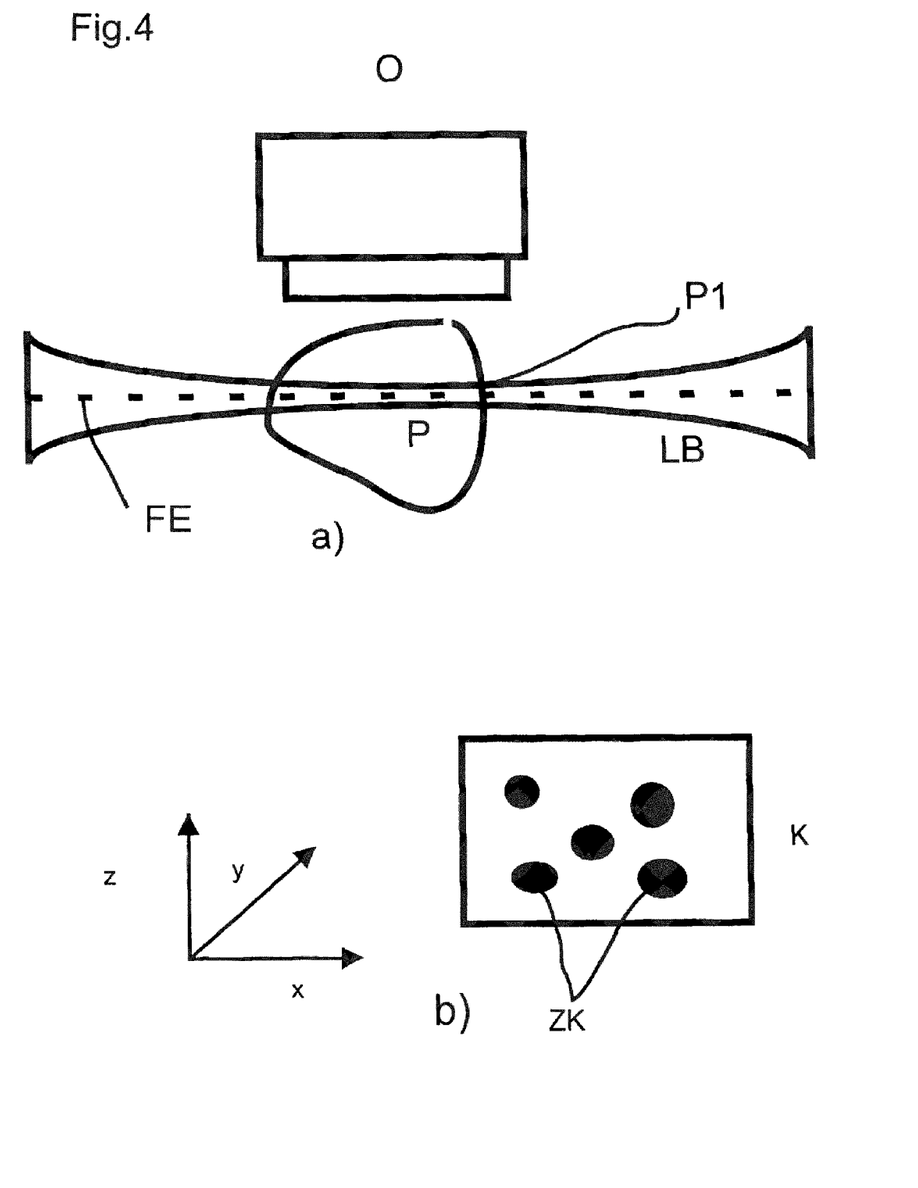
FIGS. 4 to 6 show the effects brought about by the optical characteristics of the sample that can occur
Figure 5:
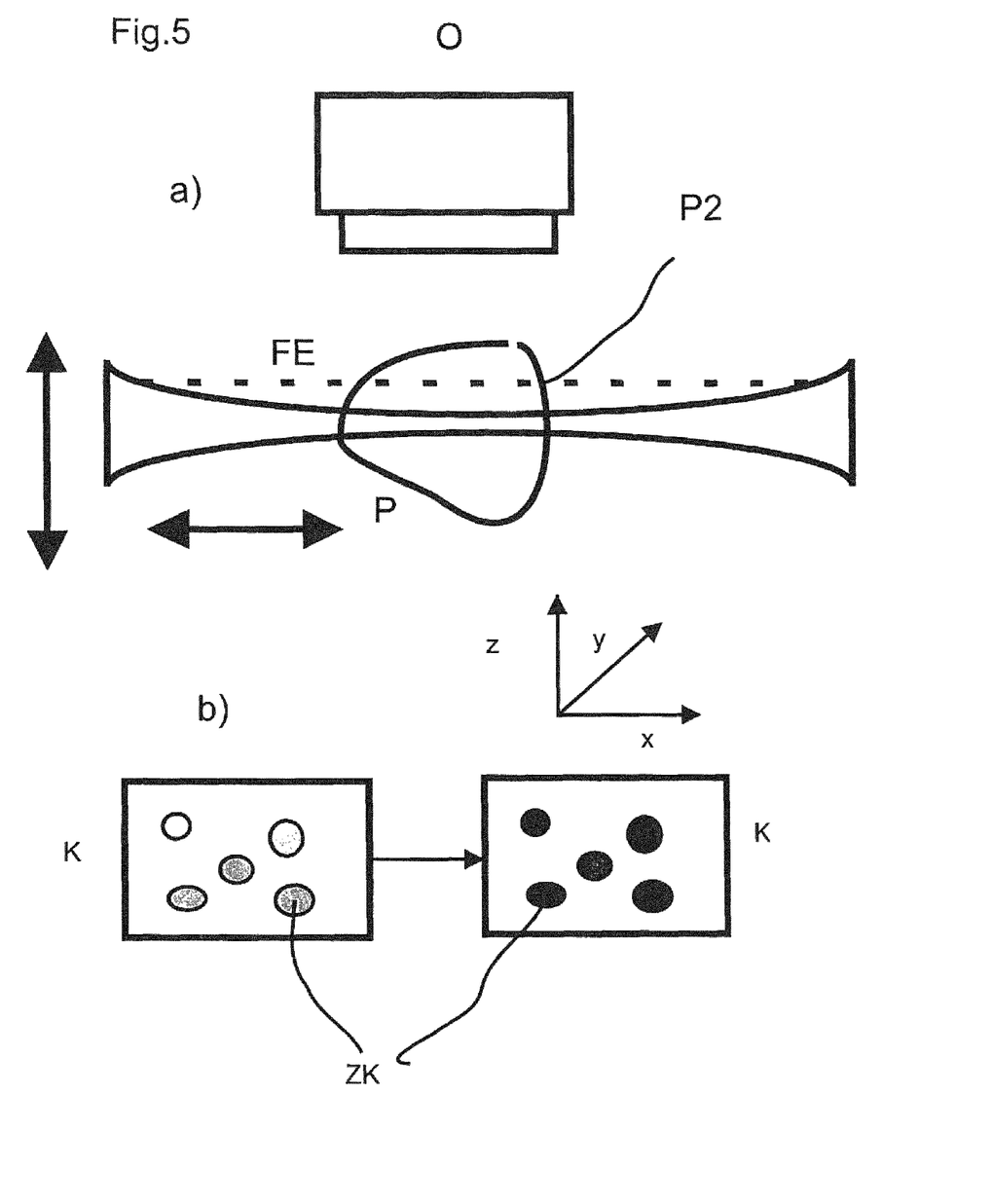
Figure 6:
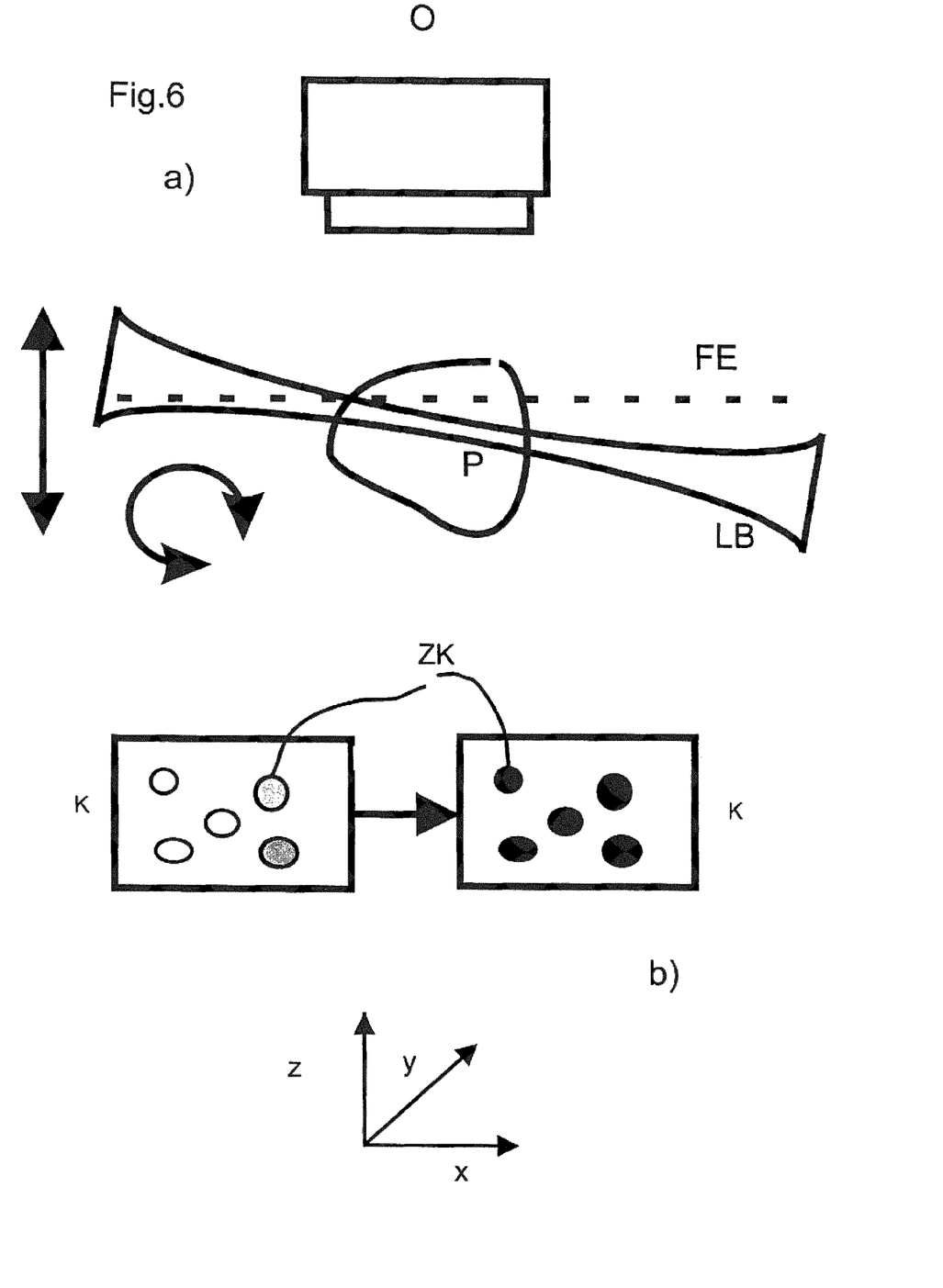

FIGS. 4 to 6 show the effects brought about by the optical characteristics of the sample that can occur, for example, during the above-mentioned capture of an image stack. For this purpose, three positions of the sample P relative to the detection objective O are shown. Any additional devices such as a sample chamber with immersion medium have been left out of the diagram. The sample can be, for example, the section of a cell tissue in which the cell nuclei have been made visible through a fluorescent marker.

In the position according to 4a) and b), the region of the light sheet illumination completely overlaps the focal plane of the detection objective such that the cell nuclei ZK located in the focal plane of the detection optics are registered with approximately the same contrast in camera image K.

In the position according to 5a) and b), two effects occur owing to the optical path length which is changed due to the different sample position: first, the focal plane FE of detection shifts in z direction relative to the nominal optical axis of the illumination LB. The cell nuclei located in the focal plane can now no longer be displayed with full contrast because of the diminished overlapping with the light sheet illumination. Further, a focus shift along the x-direction can also come about in the illumination so that a corresponding image inhomogeneity can also come about due to the inhomogeneous intensity distribution in the illumination beam.

In the position shown in FIGS. 6a) and b), in addition to an expanded focus shift in the detection, a tilting of the light sheet occurs additionally because the illumination beam is correspondingly deflected at the sample surface by a discontinuity in the refractive index.

The effects described above are mentioned by way of example. Of course, the situation in the normal case is even more complex because the sample is sometimes characterized by a complicated, inhomogeneous permittivity, which can also express itself, for example, in the occurrence of a plurality of optical interfaces within the sample volume.

There are no known prior art methods which directly compensate for artifacts of this kind like the methods described above.

Further Advantageous Effects and Refinements of the Invention:

[A]

The coupled movement of light sheet and sample relative to one another greatly simplifies the manual adjustment process. In this method, the user generally evaluates the image quality visually. Owing to the fact that the user can now concentrate on the image information in a sample plane that is held stationary, the adjustment process is more intuitive and goal-oriented. The problems described above no longer occur.

[B]

A second partial aspect consists in that an automatic light sheet adjustment in real samples is possible by means of the coupled movement. The aid of a reference sample, whether embodied as a homogeneous fluorescing sample or determined reference objects such as beads, is no longer necessary. In view of the fact that the same sample plane is always utilized for evaluation because of the coupled adjusting movement, the image information that is generally present is irrelevant. The coupled movement is advantageous for all automatic adjusting processes, whether a two-dimensional light sheet or a structured light sheet is used or with evaluation of the contrast, modulation depth or PSF.

[C]

The methods of light sheet microscopy are based on the capture of an image stack (z stack) through a relative movement of the sample and focal plane of detection. Because of sample inhomogeneities or penetration depth into the sample medium, the optimal adjustment position for the light sheet depends on the z plane. An advantageous partial aspect of the invention consists in that object-specific inhomogeneities of different sample planes which require a different optimal adjustment position depending on plane can be calibrated out by the coupled movement and, therefore, also by the applicability of the adjusting process to all samples, particularly real samples. This method is configured in the following way, for example:

1. The optimal adjustment position for a subset of z planes (sample planes) is determined by means of the preferred evaluation algorithm within the real sample.
2. The optimal adjustment position for the z planes between these sample planes is interpolated via a suitable function (polynomic, spline, . . . ).
3. While the z stack is being captured, the specific optimal adjustment position of the light sheet is adjusted for every z plane. This also corresponds to a coupled movement, for example, of sample and light sheet. In particular, this can also entail an angular adjustment (see FIG. 6).
4. A z stack with optimal image quality is achieved by the optimal adjustment position for each individual image plane.
5. Any distortions in the total 3D image of the sample occurring through light sheet tracking are computationally corrected in addition.

[D]

The methods of light sheet microscopy are further based on the fact that the reconstruction of a 3D image is possible through a relative rotation of the sample with respect to the detection direction and illumination direction and the subsequent capture of a plurality of z stacks at different angles (views). For an optimal image result it is also important in this respect that the optimal adjustment position of the light sheet is adjusted for every individual illumination direction, since the penetration depth and the optical characteristics of the sample differ from each illumination direction. This is only possible by means of a simultaneous and successively executed movement of the sample and light sheet.

[E]

An improved image result is achieved when partial aspect [B], partial aspect [C] and partial aspect pi are combined.

[F]

In a z stack and/or a multiview capture, a changed focus deviation in the illumination direction relative to the image field can also come about through movement of the sample. Consequently, a corresponding tracking of the light sheet position in x direction may be advantageous. Of course, this can also be coupled with the described movement in z direction.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method for SPIM microscopy with a microscope comprising:
   an illumination device comprising:
      an illumination light source; and
      an illumination beam path for illuminating a sample with a light sheet;
   a detection arrangement configured to detect light which is radiated from the sample with a detection objective; and
   an adjusting means configured to adjust the illumination beam path at least along the optical axis of the detection objective;
   wherein the light sheet is substantially planar in a focus of the detection objective or of a defined plane in a vicinity of a focus of the imaging detection objective;
   wherein the detection objective has an optical axis which intersects the plane of the light sheet at a non-zero angle;
   wherein the sample and the light sheet are moved relative to each other in direction of the optical axis of the detection objective for acquiring different sample planes; and
   wherein the method comprises:
      a first step comprising, with reference to a sample to be examined, carrying out a calibration so that the actual position and orientation of the light sheet in different sample planes is detected depending on the position and orientation of the sample and stored; and a second step comprising utilizing the stored position and orientation of the light sheet during observation and/or detection of the sample based on the values stored in the first step to correct the position and orientation of the light sheet relative to a focal plane of the detection objective.

2. The method according to claim 1;
wherein, in the second step, the position and orientation of the light sheet and/or of the detection objective is corrected or adjusted simultaneously with, or subsequent to, the relative movement of the sample.

3. The method according to claim 1;
wherein, in the second step, a detection and an evaluation of sample contrast are carried out during the relative movement.

4. The method according to claim 1;
wherein, in the second step, the relative movement takes place until a maximum image contrast is obtained or until an image contrast is optimal on the basis of criteria.

5. The method according to claim 1, further comprising:
moving the light sheet relatively around an adjusted vertical focus position and orientation of the detection objective to obtain a maximum or optimal contrast.

6. The method according to claim 1;
wherein the adjusting means is for the detection objective, for the illumination, or for both; and
wherein, in the second step, coupling of the movement of the light sheet and/or of the detection objective relative to the sample is carried out via an actuating unit which is connected to the adjusting means.

7. The method according to claim 1, further comprising:
tilting the illumination beam path around at least one axis.

8. The method according to claim 7;
wherein the at least one axis lies in the optical axis of the detection objective.

9. A microscope, control device, or
combination thereof, configured to implement the method according to claim 1.

10. A non-transitory computer readable medium comprising:
a computer program configured to implement the method according to claim 1.

11. A method for SPIM microscopy with a microscope comprising:
an illumination device comprising:
an illumination light source; and
an illumination beam path for illuminating a sample with a light sheet;
a detection arrangement configured to detect light which is radiated from the sample with a detection objective; and an adjusting means configured to adjust the illumination beam path at least along the optical axis of the detection objective;
wherein the light sheet is substantially planar in a focus of the detection objective or of a defined plane in a vicinity of a focus of the imaging detection objective;
wherein the detection objective has an optical axis which intersects the plane of the light sheet at a non-zero angle;
wherein the sample and the light sheet are moved relative to each other in direction of the optical axis of the detection objective for acquiring different sample planes; and
wherein the method comprises:
adjusting, during the relative movement of the sample, the position and orientation of the light sheet relative to the focal plane of the detection objective so that at least one of the light sheet and the detection objective executes a relative movement in at least one direction relative to the sample.

12. The method according to claim 11;
wherein the position and orientation of the light sheet and/or of the detection objective is corrected or adjusted simultaneously with, or subsequent to, the relative movement of the sample.

13. The method according to claim 11;
wherein a detection and an evaluation of sample contrast are carried out during the relative movement.

14. The method according to claim 11;
wherein the relative movement takes place until a maximum image contrast is obtained or until an image contrast is optimal on the basis of criteria.

15. The method according to claim 11, further comprising:
moving the light sheet relatively around an adjusted vertical focus position and orientation of the detection objective to obtain a maximum or optimal contrast.

16. The method according to claim 11;
wherein the adjusting means is for the detection objective, for the illumination, or for both; and
wherein coupling of the movement of the light sheet and/or of the detection objective relative to the sample is carried out via an actuating unit which is connected to the adjusting means.

17. The method according to claim 11, further comprising:
tilting the illumination beam path around at least one axis.

18. The method according to claim 17;
wherein the at least one axis lies in the optical axis of the detection objective.

19. A microscope, control device, or combination thereof, configured to implement the method according to claim 11.

20. A non-transitory computer readable medium comprising:
a computer program configured to implement the method according to claim 11.

* * * * *